(12) United States Patent
Killinger et al.

(10) Patent No.: US 8,887,656 B2
(45) Date of Patent: Nov. 18, 2014

(54) CONTAINER WITH ADJUSTABLE DATE INDICIUM

(71) Applicant: Medela Holding AG, Baar (CH)

(72) Inventors: Timothy D. Killinger, Mount Horeb, WI (US); Kevin J. Rachuk, Harvard, IL (US); Mark A. Luzbetak, Kildeer, IL (US); Jill M. Hunt, Woodstock, IL (US); Ashley Ceniceros, Chicago, IL (US); Brian J. Warren, Schaumburg, IL (US)

(73) Assignee: Medela Holding AG, Baar (CH)

( * ) Notice: Subject to any disclaimer, the term of this patent is extended or adjusted under 35 U.S.C. 154(b) by 49 days.

(21) Appl. No.: 13/670,620

(22) Filed: Nov. 7, 2012

(65) Prior Publication Data
US 2013/0062346 A1    Mar. 14, 2013

Related U.S. Application Data

(63) Continuation of application No. 12/913,499, filed on Oct. 27, 2010, now Pat. No. 8,371,464.

(51) Int. Cl.
| G09F 9/00 | (2006.01) |
| B65D 51/24 | (2006.01) |
| A61M 1/00 | (2006.01) |

(52) U.S. Cl.
CPC ............ *B65D 51/24* (2013.01); *A61M 2205/60* (2013.01); *A61M 1/0001* (2013.01); *G09F 9/00* (2013.01)
USPC ............ 116/308; 116/306; 116/309; 215/230

(58) Field of Classification Search
CPC .................................. G09F 9/00; B65D 51/24
USPC ........... 116/306–308, 327, 298–299, DIG. 1, 116/201, 309; 215/11.1, 206, 230; 40/310–311, 111, 113; 222/29
See application file for complete search history.

(56) References Cited

U.S. PATENT DOCUMENTS

| 261,131 | A | | 7/1882 | Bonshire | |
| 2,111,637 | A | * | 3/1938 | Mehaffey | 116/308 |
| 2,434,611 | A | * | 1/1948 | Hamiel | 215/11.5 |
| 2,450,949 | A | | 10/1948 | Gattuccio et al. | |
| 2,587,147 | A | * | 2/1952 | Guion et al. | 116/308 |
| 2,767,680 | A | * | 10/1956 | Lermer | 116/308 |
| 3,446,179 | A | | 5/1969 | Bender | |
| 3,766,882 | A | | 10/1973 | Babbitt, III | |
| 3,960,713 | A | * | 6/1976 | Carey | 206/534 |
| 4,345,541 | A | | 8/1982 | Villa-Real | |
| 4,365,722 | A | * | 12/1982 | Kramer | 215/220 |
| 4,432,300 | A | * | 2/1984 | Lyss | 116/308 |
| 4,482,068 | A | * | 11/1984 | Agbay et al. | 215/225 |
| 4,548,157 | A | * | 10/1985 | Hevoyan | 116/308 |
| 4,705,182 | A | | 11/1987 | Newel-Lewis | |

(Continued)

FOREIGN PATENT DOCUMENTS

WO   WO2009111765    9/2009

*Primary Examiner* — R. A. Smith
*Assistant Examiner* — Tania Courson
(74) *Attorney, Agent, or Firm* — McDonnell Boehnen Hulbert & Berghoff LLP

(57) ABSTRACT

A closure for a container has a plurality of indicia such as date and/or time, disposed on the lid's top surface, with a rotary collar which is adjustable to a fixed position to highlight (select) indicia regarding the contents of the container.

14 Claims, 15 Drawing Sheets

(56) References Cited

U.S. PATENT DOCUMENTS

| | | | |
|---|---|---|---|
| 4,802,438 A | 2/1989 | DeJonge | |
| 4,877,119 A * | 10/1989 | Hosking | 206/459.1 |
| 4,920,912 A | 5/1990 | Kirkling | |
| 5,082,129 A | 1/1992 | Kramer | |
| 5,184,739 A * | 2/1993 | Kusz | 215/220 |
| 5,242,067 A | 9/1993 | Garby et al. | |
| 5,261,548 A | 11/1993 | Barker et al. | |
| 5,284,262 A * | 2/1994 | O'Nan | 215/206 |
| 5,297,687 A | 3/1994 | Freed | |
| 5,299,701 A | 4/1994 | Barker et al. | |
| 5,358,117 A * | 10/1994 | Adams | 206/534 |
| 5,586,087 A * | 12/1996 | Silverson | 368/10 |
| 5,638,970 A * | 6/1997 | Garby et al. | 215/219 |
| 5,662,224 A | 9/1997 | Nogues | 206/534 |
| 5,732,836 A * | 3/1998 | Barker et al. | 215/230 |
| 5,896,990 A * | 4/1999 | Barzana | 206/459.1 |
| 6,003,467 A | 12/1999 | Shelton-Ferrell et al. | |
| 6,059,133 A | 5/2000 | Lai | |
| 6,068,149 A | 5/2000 | Telega | |
| D439,534 S | 3/2001 | Scarrott et al. | |
| D456,292 S * | 4/2002 | Scarrott et al. | D10/96 |
| D481,946 S | 11/2003 | Nicholson et al. | |
| 6,779,480 B2 | 8/2004 | Zamjahn | |
| 6,805,072 B1 * | 10/2004 | DeSano | 116/308 |
| 6,904,867 B2 | 6/2005 | Zamjahn | |
| 7,222,736 B1 | 5/2007 | Seijas | |
| 7,555,995 B1 * | 7/2009 | Stump et al. | 116/311 |
| 7,556,151 B2 | 7/2009 | Seijas | |
| 7,584,712 B2 | 9/2009 | Lu | |
| 7,661,384 B2 | 2/2010 | Mataya | |
| 7,665,611 B2 | 2/2010 | Koch | |
| 7,857,134 B2 | 12/2010 | Koch | |
| 7,878,350 B2 * | 2/2011 | Ramoundos | 215/230 |
| 8,020,507 B2 * | 9/2011 | Strong | 116/308 |
| 8,051,997 B2 * | 11/2011 | Buckley | 215/230 |
| 8,074,643 B2 * | 12/2011 | Scarrott et al. | 128/200.23 |
| 8,136,687 B2 * | 3/2012 | Wu | 220/254.1 |
| 8,220,629 B2 * | 7/2012 | Crosby | 206/385 |
| 8,534,220 B1 * | 9/2013 | Olson | 116/309 |
| 8,689,988 B2 * | 4/2014 | Xu et al. | 215/230 |
| 2003/0000452 A1 | 1/2003 | Zamjahn | |
| 2003/0192468 A1 | 10/2003 | Goertzen | |
| 2004/0206295 A1 | 10/2004 | Zamjahn | |
| 2006/0180566 A1 | 8/2006 | Mataya | |
| 2006/0213858 A1 | 9/2006 | Kraus et al. | |
| 2007/0056502 A1 | 3/2007 | Lu | |
| 2007/0187282 A1 | 8/2007 | Seijas | |
| 2007/0248721 A1 | 10/2007 | Strong | |
| 2008/0000792 A1 | 1/2008 | Koch | |
| 2008/0099423 A1 | 5/2008 | Koch | |
| 2009/0120898 A1 | 5/2009 | Hunt et al. | |
| 2009/0139950 A1 | 6/2009 | Greter et al. | |
| 2009/0178940 A1 * | 7/2009 | Said | 206/221 |
| 2009/0314733 A1 | 12/2009 | Pfenniger et al. | |
| 2009/0314734 A1 | 12/2009 | Pfenniger et al. | |
| 2009/0314736 A1 | 12/2009 | Rigert et al. | |
| 2010/0140204 A1 | 6/2010 | Vischer | |

\* cited by examiner

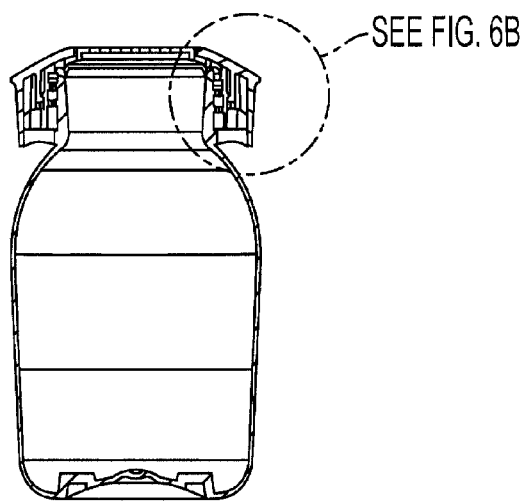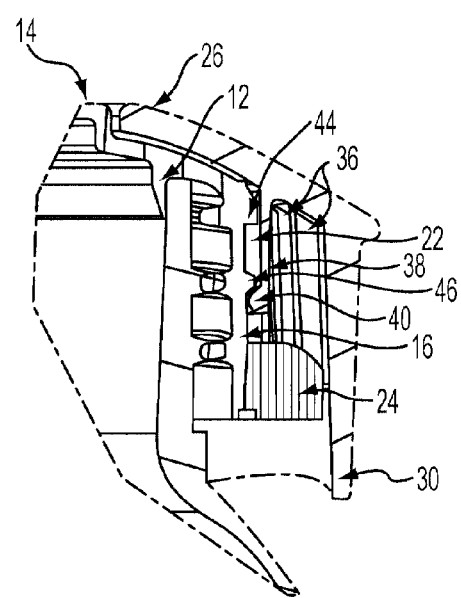
FIG. 6A
FIG. 6B

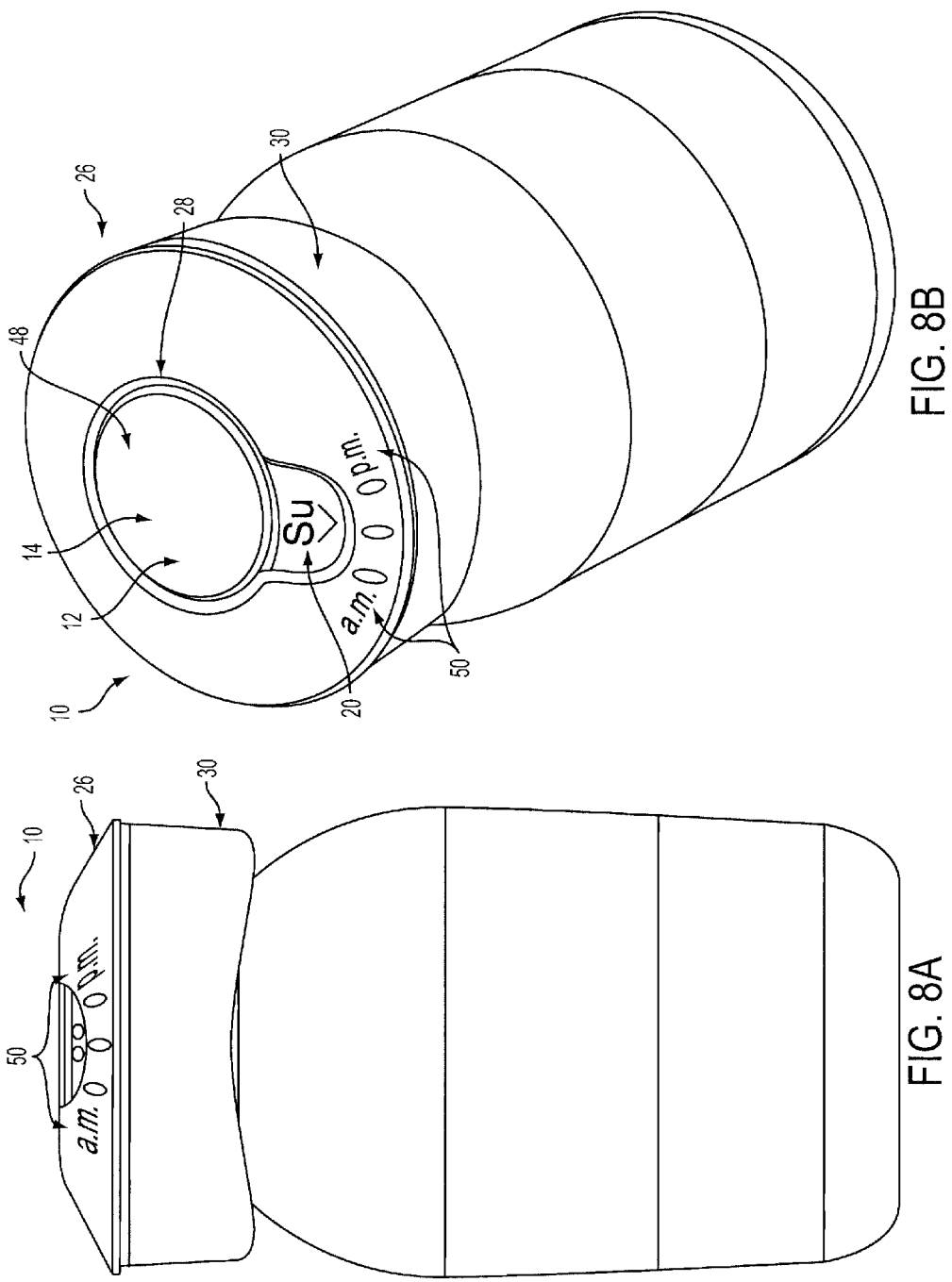

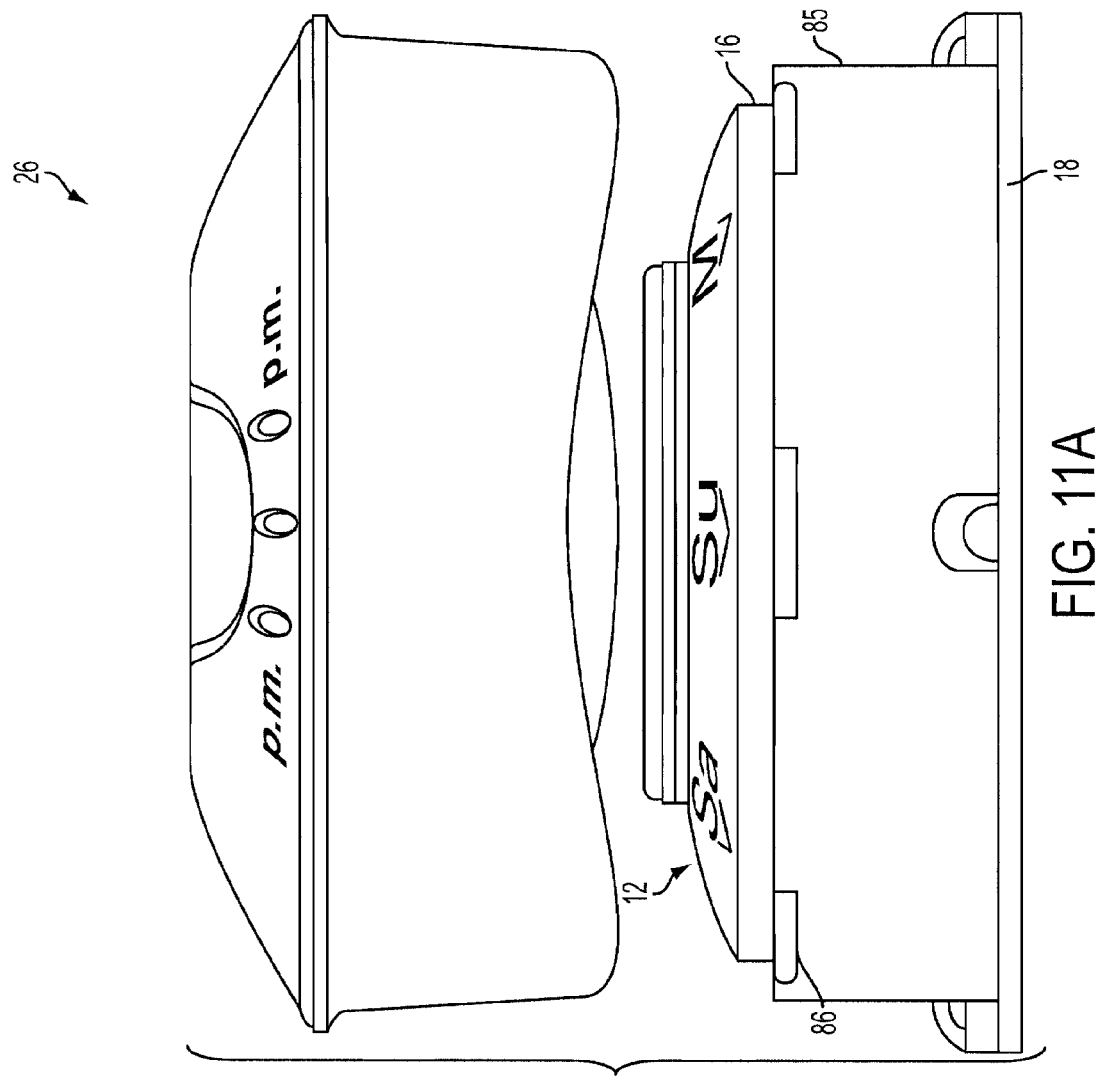
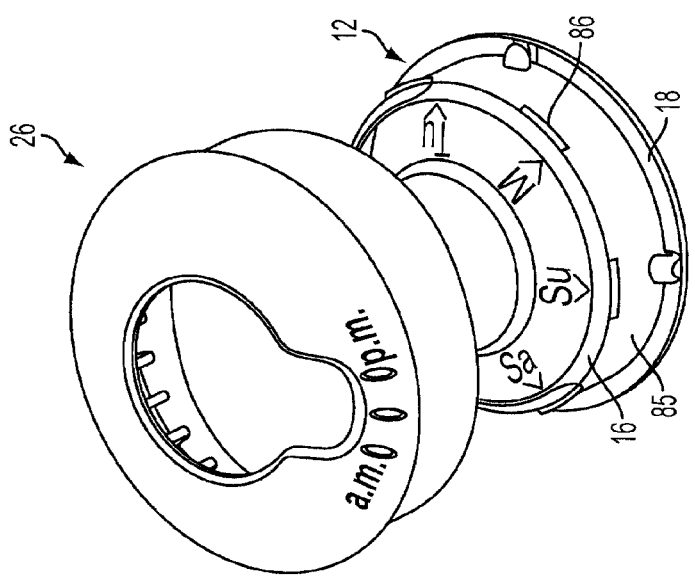
FIG. 11A
FIG. 11B

CONTAINER WITH ADJUSTABLE DATE INDICIUM

PRIORITY CLAIM

This application is a continuation of U.S. Ser. No. 12/913,499 filed Oct. 27, 2010.

BACKGROUND OF THE INVENTION

Breast milk may be stored in a refrigerator, such as for five to seven days. Frozen breast milk may be stored in a freezer, such as for up to six months. Containers of stored human breast milk are often desired to be identified by a day and even time of the day when the milk was expressed, which may indicate first, second, and third pumping sessions, or first, second, and third feeding of the day, etc. Some common labeling methods include a hand-made label from masking tape, a manufactured adhesive labeling material, or a piece of paper held to the side of the container with a rubber band. Tape and adhesive labels create a problem in that they must be overwritten or removed for reuse of the container. Rubber bands break, or lose the attached note. These labeling methods thus could stand improvement.

SUMMARY OF THE INVENTION

In accordance with significant objectives of the invention, a novel container allows the user a means of readily indicating identifying information related to the contents of the container, such as day and time of day, when the contents were put into the container, or put in storage, or some other event associated with the contents. Preferably, the container closure includes indicia that are variously selectable by the user for repeated use of the container with changing of the indicia from time to time.

In one form, the invention may be attached to a cap or cap-like closure for the container. It may be an original part of the container, or act as a replacement for a container's preexisting closure. Whichever, the invention may be applied to a container or product in a manner appropriate to the product and application. For instance, the invention could be part of or associated with a carton or bag, but not necessarily as a closure therefor. However, in its preferred form, the invention is most typically going to be as part of the closure.

The intended use of the invention is to provide the user and end user with an easy labeling solution that is intuitive (easy to use), less labor intensive, and less prone to error or interpretations, among other things. While described herein in the environment of breastmilk expression, storage and feeding, the use of this invention is not limited only to the storage of breast milk. Additionally, there are aspects of the invention directed to self-tolerancing features, to accommodate dimensional changes which may occur due to, but not limited to, multiple washing cycles, environment, normal wear, etc. The invention can allow for dimensional changes that may occur between mating components.

Thus, in a first aspect of the invention, a closure for a container comprises: (a) a lid with a top surface, a substantially cylindrical sidewall and a flange, wherein a plurality of date indicia are disposed on the lid's top surface, and wherein the sidewall defines an annular channel; (b) one or more ridges are disposed on the flange; (c) a collar, wherein the collar defines an aperture, through which the date indicia will be variously and selectably visible when the collar is associated with the lid through a rotary mounting thereof, the collar further having an exterior wall with an inner surface and an outer surface; (d) a plurality of channels formed on the collar exterior wall's inner surface; and (e) one or more tongues extending from the collar exterior wall's inner surface, with a detent formed at a free end of each of the one or more tongues that can engage in the lid's sidewall annular channel. When so engaged, the collar is freely rotatable to select a date on the lid by locating the date in the aperture (window) of the collar. The collar is then moved axially relative to the lid, thereby taking the detent out of the annular channel, and engaging a latching mechanism between the lid and collar to fix the date indicium in the aperture.

The invention further contemplates a closure for a container including a lid having a top surface and a substantially cylindrical sidewall, with an annular channel formed in the lid sidewall. Indicia indicative of differing dates and/or times are provided on the lid. Note that the indicia could be days of the week, months, time or even some other kind of temporal indicator related to the contents of the container. Indeed, the indicia need not be just of a temporal nature, so long as they are selectable in the manner described.

A collar is associated with the foregoing lid. The collar fits onto the lid on a common central axis. The collar has a see-through area formed therein, which could be an aperture, a transparent area, a window, or the like, which will function to locate an indicium therein. The collar further has a sidewall with an inner surface facing the lid sidewall when the collar is mounted to the lid.

In this embodiment, at least one flexible member extends from the collar toward the lid sidewall. Preferably, the flexible member includes a part engaging within the annular channel of the lid in the first position, wherein the collar is rotatable about the lid. There is a second position wherein the collar is moved axially, with the detent then being moved out of the annular channel of the lid. In this second position, a latching mechanism between the collar and the lid becomes engaged, which latches the collar in place in the second position, with the chosen indicium/indicia visible through the see-through area of the collar, the indicium having been selected through rotation of the collar on the lid when in the first position.

Put perhaps even more broadly, a contents indicator for a container is provided having a base with indicia thereon indicative of differing dates and/or times. A selector part is rotatably mounted with the base, the selector part having a common central axis with the base and a see-through area formed therein (such as on a top, or in a sidewall). The selector part sidewall has an inner surface facing a base sidewall.

The selector part has a first position wherein it is rotatable about the base, and a second position wherein it is moved axially of the base into a latching condition.

A latching mechanism is between the selector part and the base which latches the selector part in place in the second position, whereby the date and/or time indicia are variously visible through the see-through area of the selector part and selectable through rotation of the selector part on the base when in the first position.

The foregoing embodiment advantageously has an upper ring and a lower ring on the base (e.g., lid), sidewall, which rings are concentric with the axis and are respectively on opposite axial sides of a groove formed in the lid sidewall. The groove receives a flexible member therein, which extends from the selector part. The upper ring forms a stop for the flexible member against removal of the selector part from the lid, and the lower ring engages with the flexible member to hold the selector part in the second position.

In the same embodiment, the latching mechanism comprises a plurality of teeth located on one of the lid and the selector part. The teeth are engageable with complementary notches formed on the other of the lid and selector part when the selector part is in the second position. The lower ring has a lower edge which is engaged by the flexible member in the second position to maintain the teeth within the notches to thereby prevent rotary movement of the selector part.

The plurality of indicia may comprise a first set of indicia for a day of the week, and a second set of indicia for time of day. The time of day indicia in one form is located on the selector part adjacent the see-through area, and is selectable through location of the see-through area relative to the day indicium selected. This can be done, for instance, by having the time of day indicia (e.g., "a.m." and "p.m.") noted a little left and a little right of the center line of the see-through area, so that by canting the see-through area a little left or right of center, a time of day is indicated.

As will further be appreciated, the base and selector part need not be limited to just a rotary mounting, so long as they are relatively movable. So too, the location of the indicia and the selector for the indicia could be switched, such that one of the base and the selector part has indicia thereon indicative of differing dates and/or times, and the other of the base and the selector part has an indicator thereon.

The latching mechanism previously discussed can likewise be reversed between the base and selector part. For instance, an embodiment provides the base having a base sidewall and the selector part having a selector part sidewall, with said sidewalls being in spaced relation with the selector part sidewall outboard to the base sidewall when the base and selector part are mounted together. One of the base sidewall or flange and the selector part sidewall will, in this form of the latching mechanism, have an annular groove formed thereon concentric with a common axis, and further include at least one flexible member extending from the other of the selector part sidewall and the base sidewall or flange, with the flexible member including a part engaging within the annular groove in the first (movable) position.

The invention further provides for a method for indicating information about the contents of a container. The method comprises providing a base, a selector part mounted with the base, such that the selector part has a first position wherein the selector part is movable relative to the base, and a second position wherein the selector part is moved into a latching condition relative to the base. One of the base and the selector part has indicia thereon indicative of differing dates and/or times, and the other of the base and the selector part having an indicator thereon. A latching mechanism is further provided between the selector part and the base which latches them in place in the second position.

A force is applied to one or both of the base and selector part to unlatch them and place them in the first position. The selector part is then rotated about the base to align the indicator with a selected indicium. Then another and opposite force is applied to one or both of the base and selector part to place the selector part in the second and latched position. In this manner, date and/or time indicia are variously selectable through movement of the selector part on the base when in the first position, with that selection maintained in the second and latched position.

The present invention will be further appreciated, and its attributes and advantages further understood, with reference to the detailed description below of examples of presently contemplated embodiments, taken in conjunction with the accompanying drawings, in which:

BRIEF DESCRIPTION OF THE DRAWINGS

FIG. 6A is an elevational cross-sectional view of an embodiment of a closure for a container, made in accordance with the invention, in the latched position;

FIG. 6B is an enlarged elevational cross-sectional detail view of a portion of the closure for a container shown in FIG. 6A;

FIG. 8A is an elevational view of a closure for a container made in accordance with the invention, with the lid and collar mated and in position on a container;

FIG. 8B is a perspective view of the closure for a container shown in FIG. 8A, with the lid and collar mated and in position on a container;

FIG. 11A is an exploded elevational view similar to that of, e.g., FIG. 2A, but of yet another different latching mechanism arrangement;

FIG. 11B is an exploded perspective view of the closure for a container of FIG. 11A;

DETAILED DESCRIPTION OF EMBODIMENTS OF THE INVENTION

Figure 1A:
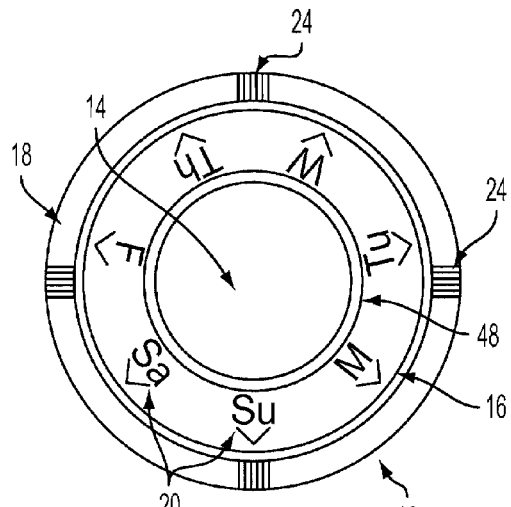
FIG. 1A is top view of an embodiment of a lid made in accordance with the invention, without a collar in place.
Figure 1D:
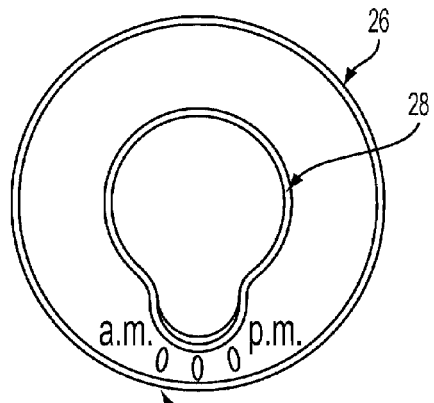
FIG. 1D is top view of a collar prior to placement on the lid shown in FIG. 1A.
Figure 1B:
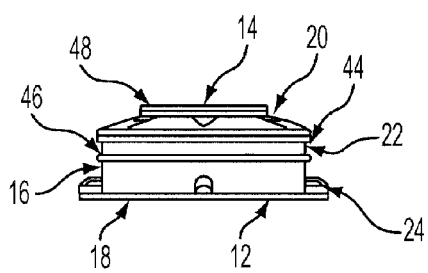
FIG. 1B is side view of the lid of FIG. 1A.
Figure 1E:
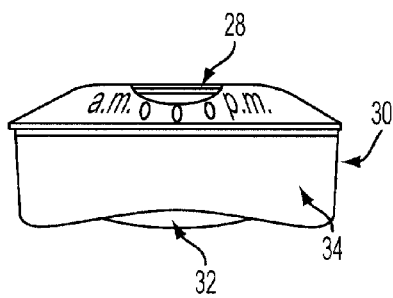
FIG. 1E is a side view of the collar shown in FIG. 1D.

In a first embodiment, as shown in FIGS. 1A-1F, a closure for a container has a lid 12 with a top surface 14, a substantially cylindrical sidewall 16 and a flange 18. A plurality of date indicia 20 are disposed on the lid's top surface 14, as by molding or printing thereon. The sidewall 16 defines an annular channel 22. One or more ridges 24 are disposed on the flange 18.

Figure 3A:
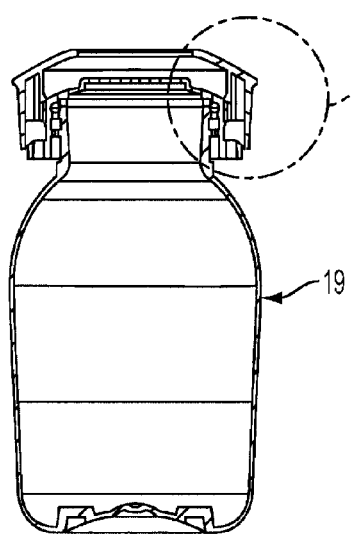
FIG. 3A is an elevational cross-sectional view of an embodiment of a closure for a container, made in accordance with the invention, in the top insertion position.
Figure 3B:
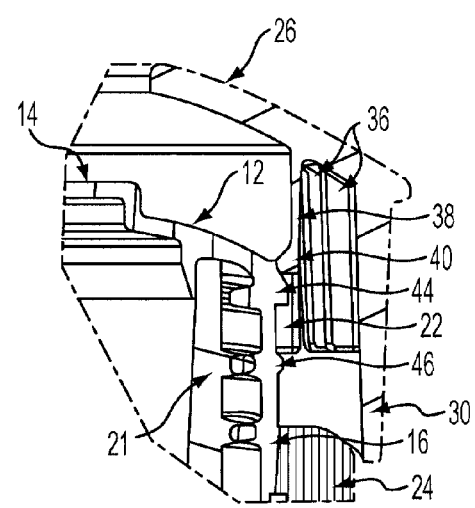
FIG. 3B is an enlarged elevational cross-sectional detail view of a portion of the closure for a container shown in FIG. 3A.

Container 19 has an upper container sidewall 21 (see, e.g., FIG. 3B).

A collar 26 has an aperture 28 in what will be the top of the closure. The collar 26 has an exterior wall 30 with an inner surface 32 and an outer surface 34. A plurality of channels 36 are formed on the exterior wall's inner surface 32. One or more tongues 38 extend from the exterior wall's inner surface 32. A detent 40 is formed at a free end of each of the tongues 38.

Figure 1C:
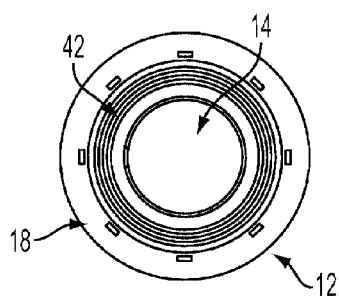
FIG. 1C is a bottom view of the lid shown in FIG. 1A.
Figure 1F:
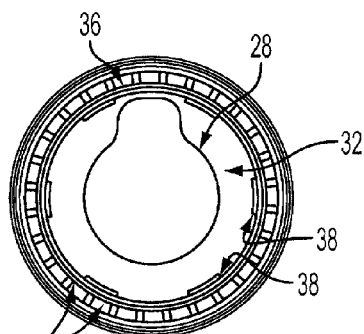
FIG. 1F is a bottom view of the collar of FIG. 1E.
Figure 2B:
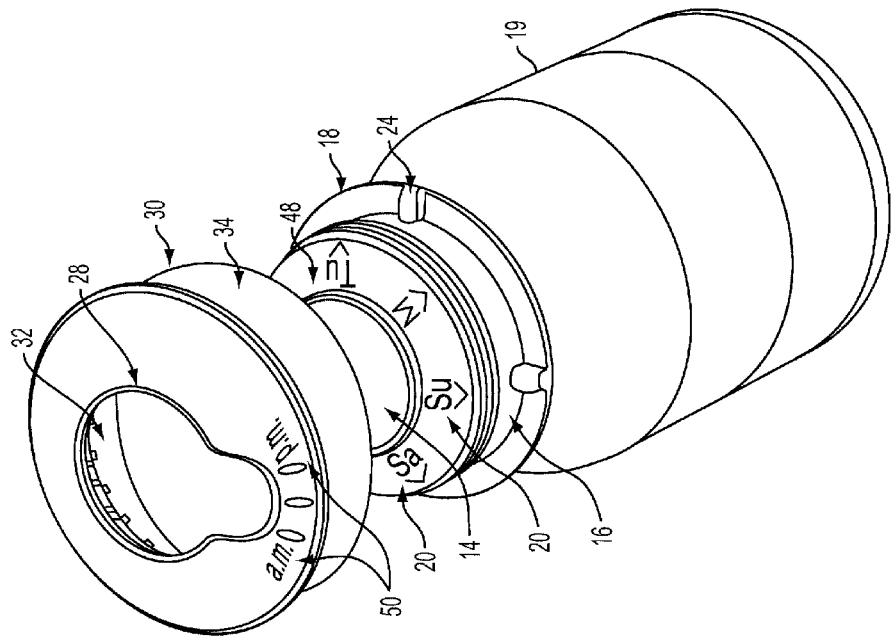
FIG. 2B is an exploded perspective view of the closure for a container of FIG. 2A.
Figure 2A:
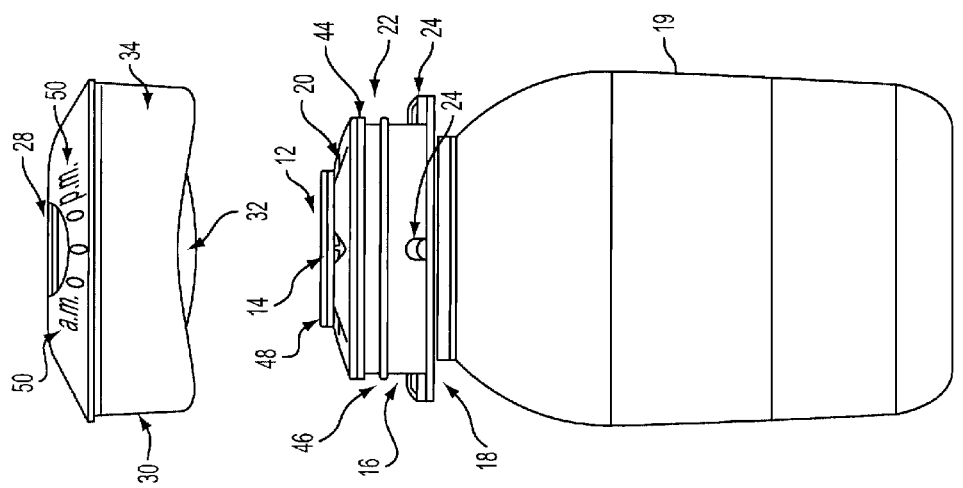
FIG. 2A is an exploded elevational view of the closure for a container made in accordance with the invention, with the lid in position on a container.

As shown in FIGS. 1C and 2A-B, the lid 12 is designed to be mated with a container through, for example, threads 42. Other attachments well-known in the art, such as a snap-fit, could be employed. The collar 26 is in place over the lid in a top insertion position, shown in FIGS. 3A-B, such that the detents 40 of each of the tongues 38 are resting against the lid's top surface 14. In one embodiment, the annular channel 22 is formed between an annular upper detent 44 and an annular lower detent 46, and the detents 40 are in contact with the upper detent 44 in the top insertion position. Force is then applied to the collar until the tongues 38 flex outwardly and the detents 40 slide over the chamfered top surface of the annular upper detent 44 and into the annular channel 22, such that the collar 26 is removably attached to the lid 12.

Figure 4A:
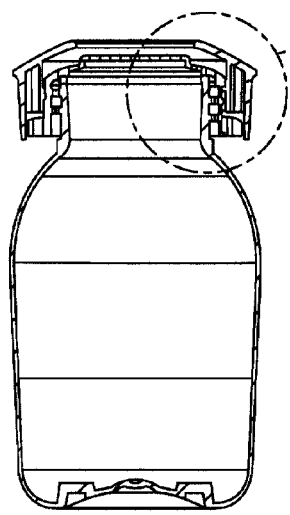
FIG. 4A is an elevational cross-sectional view of an embodiment of a closure for a container, made in accordance with the invention, in the removal stop position.
Figure 4B:
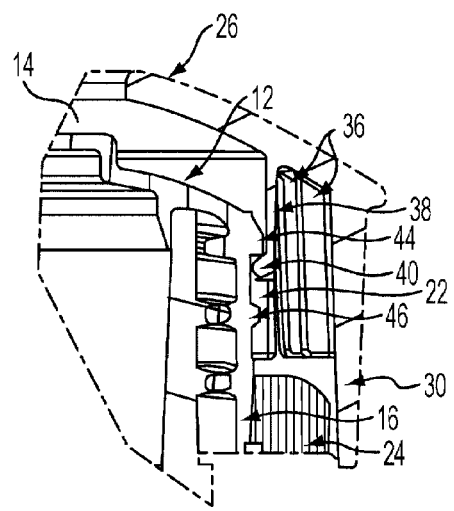
FIG. 4B is an enlarged elevational cross-sectional detail view of a portion of the closure for a container shown in FIG. 4A.
Figure 5A:
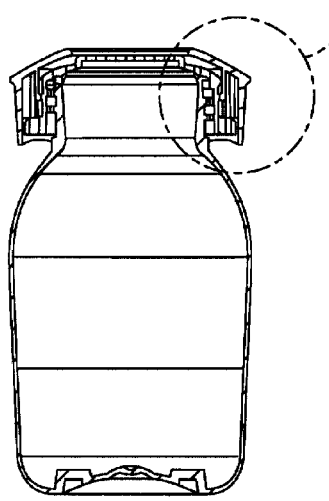
FIG. 5A is an elevational cross-sectional view of an embodiment of a closure for a container, made in accordance with the invention, in the set position.
Figure 5B:
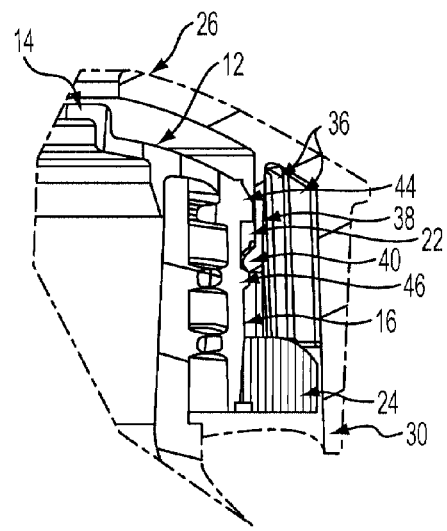
FIG. 5B is an enlarged elevational cross-sectional detail view of a portion of the closure for a container shown in FIG. 5A.
Figure 7A:
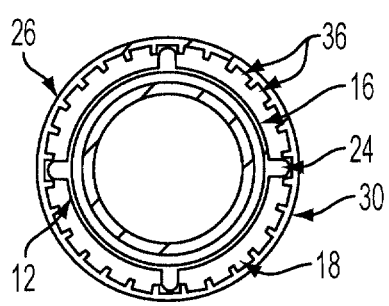
FIG. 7A is a top sectional view of a closure for a container made in accordance with the invention.
Figure 7B:
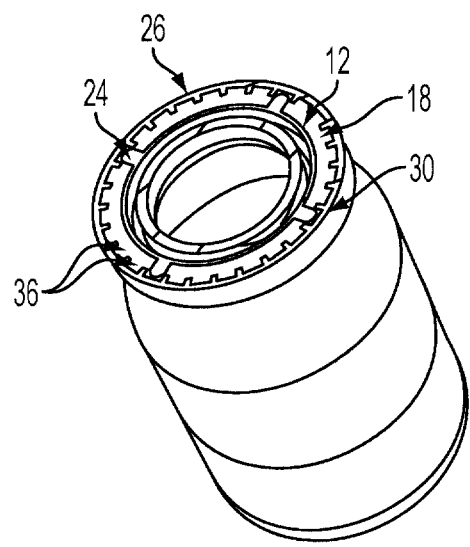
FIG. 7B is a perspective of the sectional view shown in FIG. 7A, in position on a container.

As shown in FIGS. 4A-B, the lower edge of the upper detent 44 acts as a locking detent, requiring the user to apply a greater force to separate the collar 26 from the lid 12 than is required to mate them together. When the detents 40 are disposed in the annular channel 22, shown in FIGS. 5A-B, the collar 26 is in the "set" position, and is freely rotatable about the lid 12. This allows the user to rotate collar 26 to align the aperture 28 with the appropriate date indicia 20.

The date indicia are spaced on the lid's top surface 14 relative to the one or more ridges, while the plurality of channels 36 are spaced to receive the one or more ridges 24 in a latched position, illustrated in FIGS. 6A-B. This plurality of channels 36 may be substantially equally spaced apart on the exterior wall 30. The number of channels is dependent on both the number of date indicia 20 along the top surface 14 of the lid 12 and any supplemental date indicia 50 that may appear on the collar (as discussed below).

Once the date indicium is selected, the user applies a force to the collar 26, which causes tongues 38 to flex outward and slide the detents 40 over the annular lower detent 46. The collar 26 is now in a latched position (see FIGS. 6A-B, 7A-B, and 8A-B), with the one or more ridges 24 resting within one or more of the plurality of channels 36, preventing rotation of the collar 26 about the lid 12. The width of the channels is preferably slightly larger than the width of the one or more ridges 24 to substantially prevent play or slight rotation of the collar 26 about the lid 12 in the latched position. If the user wishes to select different date indicia 20, the lower detent 46 is chamfered on both its top and bottom edges to facilitate moving the tongue detents 40 back into the "set" position in the annular channel 22.

In one embodiment, the lid 12 defines a raised portion 48 and the aperture 28 is shaped to receive the raised portion 48 in the latched position. In another embodiment, the lid 12 again defines a raised portion 48, and the collar 26 defines an opening (not shown), different from the aperture 28, that is shaped to receive the raised portion 48 in the latched position.

The plurality of date indicia 20 can comprise a first set of indicia 20 and a second set of indicia 50. The date indicia 20, 50 may comprise any indication of date or time that would be useful to track for the given contents of the container, for example, hours, minutes, dates, days of the week, morning (a.m.), evening (p.m.), etc. The collar 26 can contain the second set of date indicia 50, that preferably supplements the first set of date indicia 20 provided on the lid 12. For example, in FIGS. 1A and 1D, the lid 12 lists the days of the week 20, while the collar 26 allows the user to specify morning (a.m.) or evening (p.m.) 50 for the selected day.

In one embodiment, the interior surface 32 is discontinuous. The discontinuity may constitute a single break or many breaks that allow the interior wall to flex outwardly, when the collar 26 is attached and removed from the lid.

As noted, while the preferred form of the invention is a closure for a container, the invention could readily be adapted to some other part of the container. Thus, the lid becomes a base upon which a selector element is rotatably mounted, with other parts previously described translating into this non-closure embodiment.

Another aspect of the invention is a method using the closure of the type described, where the method comprises: (a) positioning the collar 26 over the lid 12; (b) applying a force to one or both of the collar 26 and the lid 12 until the one or more tongue detents 40 are received in the annular channel 22; (c) rotating the collar 26 about the lid 12 to align the aperture 28 over one of the plurality of date indicia 20; and (d) applying a force to one or both of the collar 26 and the lid 12 until the one or more ridges 24 are disposed between at least one of the plurality of channels 36.

Figure 9:
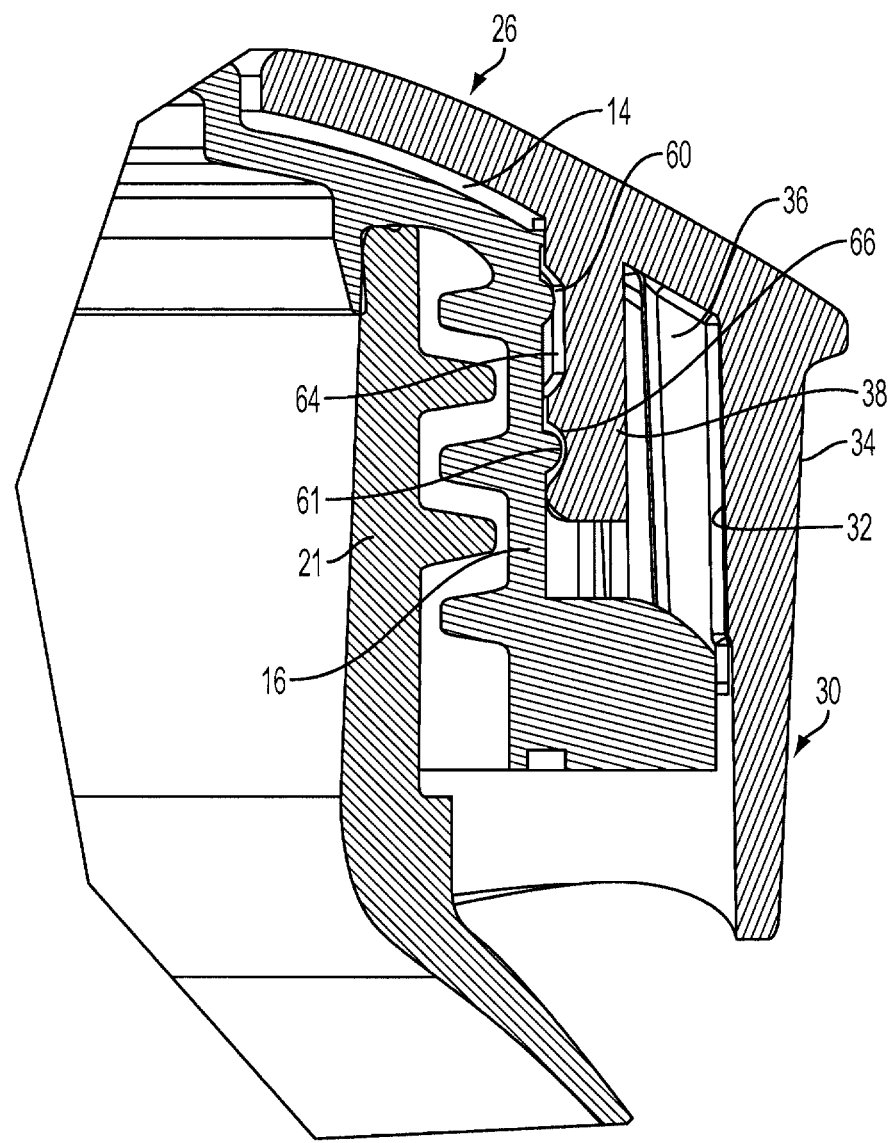
FIG. 9 is an enlarged partial sectional view similar to that of, e.g., FIG. 3B, but of a different latching mechanism arrangement.

Turning now to FIG. 9, an alternative embodiment of a latching mechanism is illustrated. Recalling that like numbers indicate like parts to those already described above, this embodiment has two detents in the form of beads 60 and 61. These beads 60, 61 are formed on the outboard side of the lid sidewall 16, and are parallel to each other and concentric with a central axis to the lid 12 and collar 26.

In this variant, the tongues 38 have an annular groove or channel 64 which receives bead 60 when the collar 26 is in the latched position. A further annular groove 66 is provided, which is more conforming to the curved outboard surface of the beads 60, 61. There are rims located above (63) and below (65) the groove 66.

It will be noted that the condition of the collar 26 relative to the lid top 14 is in the latched position in FIG. 9. Movement of the collar 26 axially upwardly (i.e., moving the collar 26 and lid 12 more apart), would place groove 66 along with rims 63, 65 in a trough formed between beads 60, 61 for free rotary movement of the collar 26 and indicium selection. Further axial movement in the same direction would place bead 60 in the groove 66, in a position to generally prevent removal of the collar from the lid.

Figure 10:
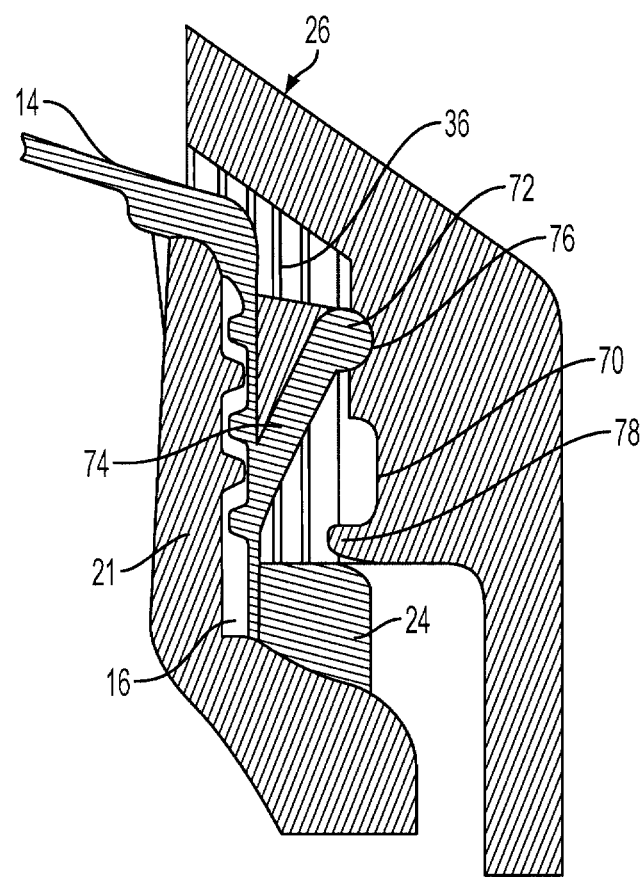
FIG. 10 is an enlarged partial sectional view similar to that of, e.g., FIG. 3B, but of yet another different latching mechanism arrangement.

FIG. 10 is yet another embodiment of a latching mechanism. Here, the general positioning of the flexible latching element with its detent, as discussed with respect to FIGS. 1 through 8, has been reversed between the collar 26 and lid 12. Accordingly, collar 26 now has an annular groove or channel 70 within which a detent bead 72 carried on the outboard side of lid sidewall 16 can selectively engage. Bead 72 is part of a crown-like element 74, which extends from a root on the sidewall 16 (FIG. 10) and upwardly and outwardly, with bead 72 around the rim thereof. Note that this crown-like element 74 may be periodically broken by sinuses or vertical gaps, to yield more flexibility to radial movement (flexing) of the bead 72 relative to the collar 26. This crown-like element 74 is essentially like an inverted and more solid (integral) form of the tongues 38 previously discussed.

As shown in FIG. 10, the bead 72 is engaged in another groove 76, which here functions much like that of groove 66 discussed in relation to FIG. 9. The lid and collar are shown in a latched condition in FIG. 10. For indicium selection, collar 26 would be moved axially upwardly to the lid top 14 (as viewed in FIG. 10), to thereby place the bead 72 within the annular groove 70 for freewheeling rotary movement of the collar 26. An enlarged shoulder 78 formed at the bottom of the annular groove 70 serves as a stop to undesired removal of the collar from the lid (as by further axial movement to separate the two).

Turning to FIGS. 11A to 11H, there is depicted yet a further embodiment modified from that of FIG. 10. Here, instead of a cantilever structure like that of crown-like element 74, a vertical wall 85 is provided. This vertical wall 85 extends from the flange 18. The bead 72 is shown here in the form of a series of beads 86 spaced on the outboard side of the vertical wall near the top thereof. Note that this vertical wall 85 could likewise be a series of vertical tongues, spaced about the flange 18.

Figure 11C:
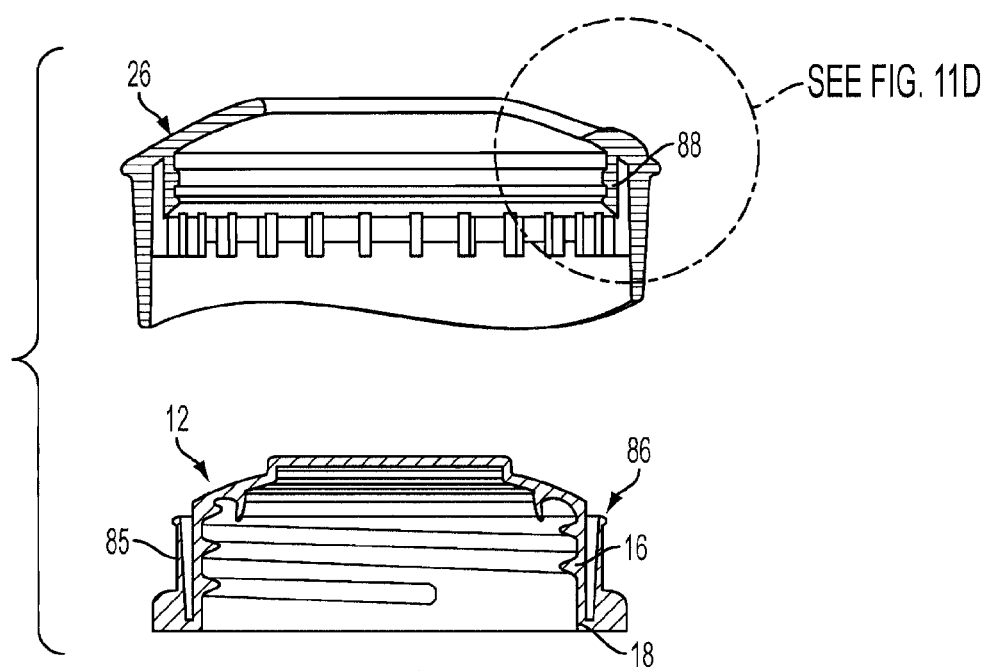
FIG. 11C is an exploded elevational, cross-sectional view similar to that of, e.g., FIG. 3A, (without the container) of the embodiment of FIG. 11A.
Figure 11D:
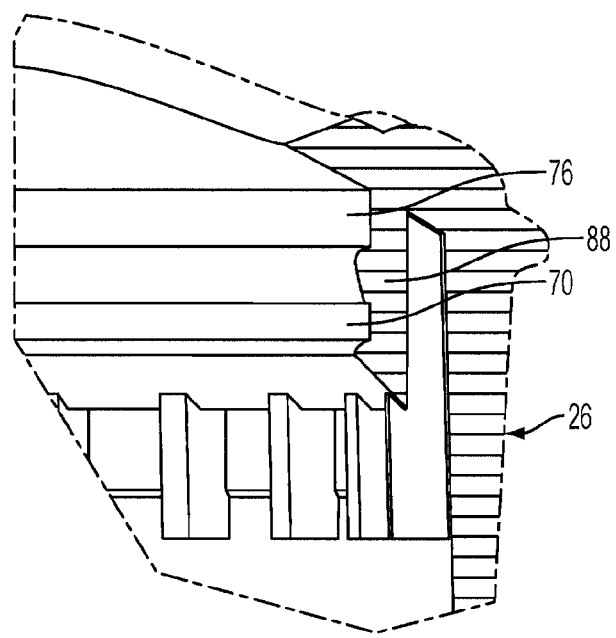
FIG. 11D is an enlarged elevational cross-sectional detail view of a portion of the closure for a container shown in FIG. 11C.
Figure 11E:
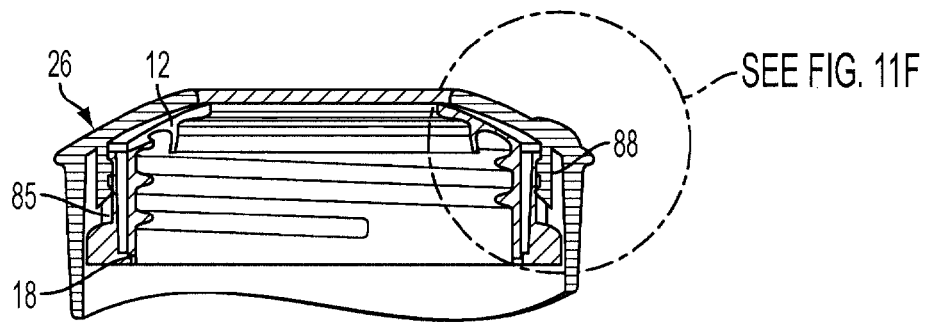
FIG. 11E is a cross-sectional view of the closure mechanism arrangement of FIG. 11A combined together in a latched condition.
Figure 11F:
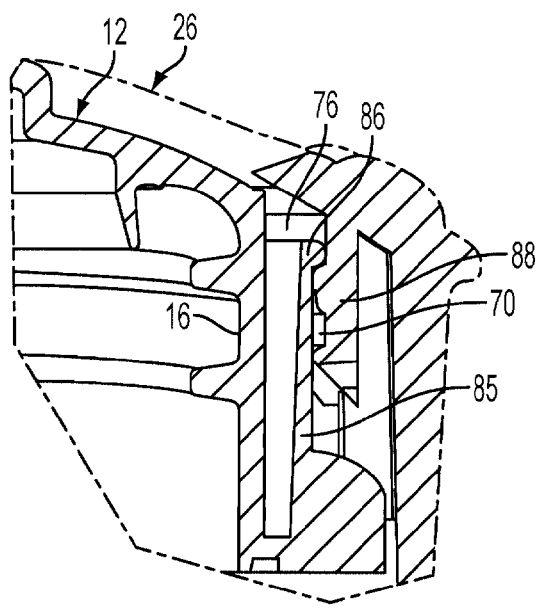
FIG. 11F is an enlarged elevational cross-sectional detail view of a portion of the closure for a container shown in FIG. 11E.
Figure 11G:
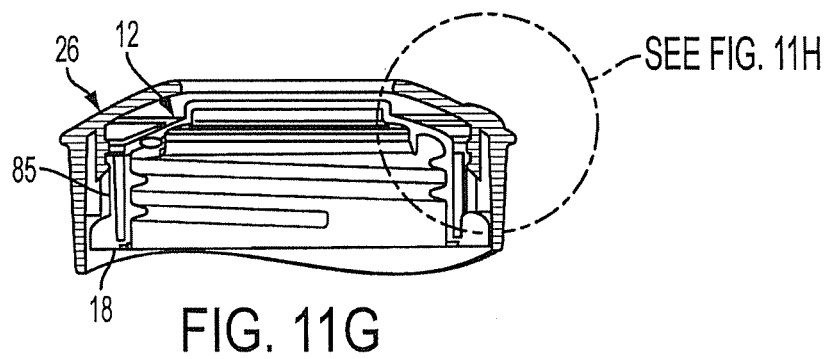
FIG. 11G is a cross-sectional view similar to that of, e.g., FIG. 11E in the set position.
Figure 11H:
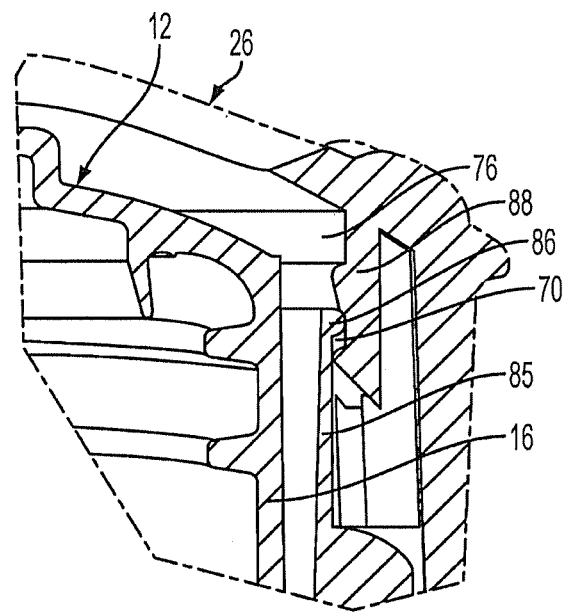
FIG. 11H is an enlarged elevational cross-sectional detail view of a portion of the closure for a container shown in FIG. 11G.

The collar 26 in this embodiment has a depending wall 88 having an annular groove or channel 70 and another groove 76 like those previously described with these numbers. In terms of function, the vertical wall 85 with its beads 86 interacts with the depending wall 88 of the collar substantially in the same manner as described with respect to the FIG. 10 embodiment. Note that FIG. 11E shows this embodiment in a latched condition, while FIG. 11G shows it in the set position (for setting the date/time indicium).

Figure 12:
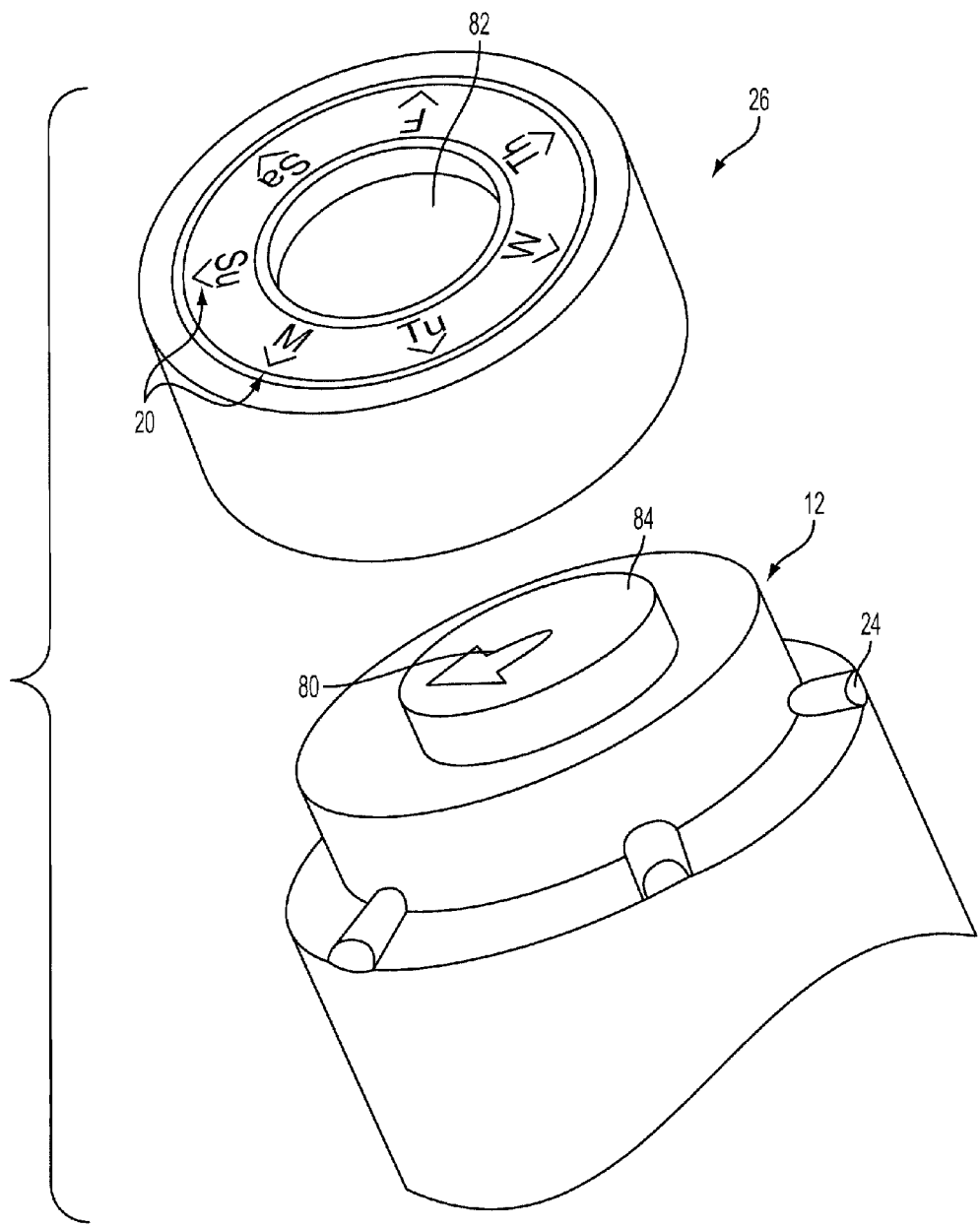
FIG. 12 is a view similar to that of FIG. 2B, but showing a modified embodiment with the indicia and indicator reversed in presentation on the lid and collar.

Now turning to FIG. 12, this embodiment simply illustrates how the date indicium 20 can be provided on the collar 26, instead of on the lid or base 12, as in previously discussed embodiments. An indicator for the selector is shown as an arrow 80, which is provided on the lid top 84. Collar 26 fits over the lid top 84 in a manner as previously described, except here the lid top 84 has been slightly modified (from lid top 14) so that the lid top 84 extends through an enlarged opening or aperture 82 formed in the collar. Lid top 84, of course, could be flush with the collar top, or below the collar top, or even visible through a transparent area provided in the collar top; the point is that the indicator 80 can be seen in use, and aligned with a selected indicium 20. A latching mechanism between the collar 26 and the lid 12 of a type previously described above would be used with this embodiment.

Note that many aspects of the foregoing embodiments may be combined together to practice the claimed invention. Thus, while a multitude of embodiments have been variously described herein, those of skill in this art will recognize that different embodiments show different potential features and designs that can be used in the other embodiments. Even more variations, applications and modifications will still fall within the spirit and scope of the invention, all as intended to come within the scope of the following claims.

The invention claimed is:

1. A contents indicator for a container, comprising:
   a base having a base sidewall, said base having indicia thereon indicative of differing dates and/or times;
   a selector part rotatably mounted with said base, said selector part having a common central axis with said base and a see-through area formed therein, wherein said selector part has a sidewall that is disposed outboard to the base sidewall, wherein one of said base sidewall and said selector part sidewall has an annular channel formed thereon concentric with a common axis, wherein at least one flexible member extends from the other of said selector part and said base, wherein said flexible member comprises a part configured to engage with said annular channel in said first position and configured to be disengaged from said annular channel in said second position;
   said selector part configured to be axially movable relative to said base between a first position and a second position, wherein said selector part is freely rotatable about said base in said first position, and wherein said selector part is in a latched condition relative to said base in said second position such that rotary movement of said selector part is prevented; and
   a latching mechanism between said selector part and said base which latches said selector part in place in said second position, whereby said date and/or time indicia are variously visible through said see-through area of said selector part and selectable through rotation of said selector part on said base when in said first position.

2. The contents indicator of claim 1, wherein said annular channel is formed on said base sidewall, wherein said annular channel is a groove, and wherein said at least one flexible member extends from said selector part toward said base sidewall.

3. The contents indicator of claim 1, wherein said annular channel is formed on said base sidewall, wherein said base sidewall has an upper ring and a lower ring which are concentric with said common axis and define a groove, said upper ring forming a stop for said flexible member against removal of said selector part from said base, said lower ring engaging with said flexible member in said second position thereby holding said selector part and said base in said second position.

4. The contents indicator of claim 3, wherein said selector part is in an indicia-set position when said part of said flexible member is positioned in said annular groove, and said latching mechanism comprises a plurality of teeth located on one of said base and said selector part engageable with complementary notches formed on the other of said base and selector part when said selector part is in said second position, said lower ring having a lower edge which is engaged by a detent of said flexible member in said second position to maintain said teeth within said notches to thereby prevent rotary movement of said selector part.

5. The contents indicator of claim 1, wherein said plurality of indicia comprises a first set of indicia for a day of the week, and a second set of indicia for time of day, said time of day indicia being located on said selector part adjacent said see-through area and being selectable through location of said see-through area relative to said day indicium selected.

6. A contents indicator for a container, comprising:
   a base;

a selector part mounted with said base, wherein said selector part has a sidewall that is disposed outboard to the base sidewall, wherein said selector part is configured to move axially relative to said base between a first position and a second position, wherein said selector part is freely rotatable relative to said base in said first position, and wherein said selector part has a latched condition relative to said base in said second position such that rotary movement of said selector part is prevented;

one of said base sidewall and said selector part sidewall having an annular channel formed thereon concentric with a common axis, wherein at least one flexible member extends from the other of said selector part and said base, wherein said flexible member comprises a part configured to engage with said annular channel in said first position and configured to be disengaged from said annular channel in said second position;

one of said base and said selector part having indicia thereon indicative of differing dates and/or times, and the other of said base and said selector part having an indicator thereon;

a latching mechanism between said selector part and said base which latches said selector part in place relative to said base in said second position, whereby said date and/or time indicia are variously selectable through movement of said selector part on said base when in said first position.

7. The contents indicator of claim 6, wherein said annular channel is formed on said base sidewall, wherein said annular channel is a groove, and wherein said at least one flexible member extends from said selector part sidewall.

8. The contents indicator of claim 6, wherein said annular channel is formed on said base sidewall, wherein said base sidewall has an upper ring and a lower ring which are concentric with said common axis and define a groove, said upper ring forming a stop for said flexible member against removal of said selector part from said base, said lower ring engaging with said flexible member in said second position thereby holding said selector part and said base in said second position.

9. The contents indicator of claim 8, wherein said selector part is in an indicia-set position when said part of said flexible member is positioned in said annular groove, and said latching mechanism comprises a plurality of teeth located on one of said base and said selector part engageable with complementary notches formed on the other of said base and selector part when said selector part is in said second position, said lower ring having a lower edge which is engaged by said detent of said flexible member in said second position to maintain said teeth within said notches to thereby prevent movement of said selector part.

10. The contents indicator of claim 6, wherein said plurality of indicia comprises a first set of indicia for a day of the week, and a second set of indicia for time of day, said time of day indicia being located on said selector part adjacent a see-through area and being selectable through location of said see-through area relative to said day indicium selected.

11. The contents indicator of claim 6, wherein said selector part has said indicia thereon and said base has said indicator alignable with said indicia thereon.

12. The contents indicator of claim 6, wherein said base has said indicia thereon, and said indicator has a see-through area formed thereon alignable with said indicia.

13. The contents indicator of claim 6, wherein said base is a closure lid for a container, and said selector part is a collar rotatably mounted about a common axis with said lid.

14. The contents indicator of claim 13, wherein said lid has a lid sidewall and said collar has a collar sidewall with said sidewalls being in spaced relation with said collar sidewall outboard to said lid sidewall when said collar and lid are mounted together, one of said collar sidewall and said lid sidewall having an annular groove formed thereon concentric with said axis, and further including at least one flexible member extending from the other of said collar sidewall and said lid sidewall with said flexible member including a part engaging within said annular groove in said first position.

* * * * *